United States Patent
Sinofsky et al.

(10) Patent No.: US 6,626,900 B1
(45) Date of Patent: Sep. 30, 2003

(54) INTRALUMENAL CONTACT SENSOR

(75) Inventors: Edward L. Sinofsky, Dennis, MA (US); Norman E. Farr, Monument Beach, MA (US)

(73) Assignee: CardioFocus, Inc., Norton, MA (US)

( * ) Notice: Subject to any disclaimer, the term of this patent is extended or adjusted under 35 U.S.C. 154(b) by 0 days.

(21) Appl. No.: 09/616,275

(22) Filed: Jul. 14, 2000

Related U.S. Application Data

(63) Continuation-in-part of application No. 09/602,420, filed on Jun. 23, 2000, which is a continuation-in-part of application No. 09/357,355, filed on Jul. 14, 1999.

(51) Int. Cl.$^7$ .............................. A61B 18/18
(52) U.S. Cl. .................. 606/15; 606/7; 356/614; 356/622; 128/898
(58) Field of Search ................... 606/3, 13–18, 606/7, 9; 600/108, 109, 112–118; 604/49, 915; 128/898; 356/614, 622

(56) References Cited

U.S. PATENT DOCUMENTS

| | | | |
|---|---|---|---|
| 4,625,724 A | 12/1986 | Suzuki et al. | 128/303.1 |
| 4,701,166 A | 10/1987 | Groshong et al. | 604/247 |
| 4,718,417 A * | 1/1988 | Kittrell et al. | 128/303.1 |
| 4,878,725 A | 11/1989 | Hessel et al. | 350/96.15 |
| 5,071,417 A | 12/1991 | Sinofsky | 606/8 |
| 5,078,681 A | 1/1992 | Kawashima | 604/53 |
| 5,090,959 A * | 2/1992 | Samson et al. | 604/96 |
| 5,125,925 A | 6/1992 | Lundahl | 606/15 |
| 5,242,438 A | 9/1993 | Saadatmanesh et al. | 606/15 |
| 5,261,904 A | 11/1993 | Baker et al. | 606/17 |
| 5,350,375 A * | 9/1994 | Deckelbaum et al. | 606/7 |
| 5,368,564 A | 11/1994 | Savage | 604/95 |
| 5,464,404 A | 11/1995 | Abela et al. | 606/15 |
| 5,507,725 A | 4/1996 | Savage et al. | 604/95 |
| 5,725,522 A * | 3/1998 | Sinofsky | 606/8 |
| 5,800,482 A | 9/1998 | Pomeranz et al. | 607/101 |
| 5,830,209 A | 11/1998 | Savage et al. | 606/15 |
| 5,833,682 A | 11/1998 | Amplatz et al. | 606/15 |
| 5,845,646 A * | 12/1998 | Lemelson | 128/898 |
| 6,071,302 A * | 6/2000 | Sinofsky et al. | 607/88 |

* cited by examiner

Primary Examiner—Linda C. M. Dvorak
Assistant Examiner—Ahmed Farah
(74) Attorney, Agent, or Firm—Thomas J. Engellenner; Tram Anh T. Nguyen; Nutter McClennen & Fish LLP

(57) ABSTRACT

An apparatus and method for phototherapy are described in which laser light or other radiation is projected from within a catheter, through a balloon member, and toward the surface of tissue. The light reflected from body fluids or the tissue surface is captured by a collecting device located within the catheter, e.g., within the balloon member, and the intensity of the reflected light is ascertained. The apparatus and method provides for accurately positioning the apparatus against the tissue treatment site.

6 Claims, 4 Drawing Sheets

INTRALUMENAL CONTACT SENSOR

RELATED APPLICATIONS

This application claims priority to U.S. Serial Number 09/602,420, filed Jun. 23, 2000, entitled "Phototherapeutic Waveguide Apparatus", attorney docket number 101327-147, now allowed, which claims priority to U.S. patent application Ser. No. 09/357,355 filed on Jul. 14, 1999, the contents of which are incorporated herein by reference.

BACKGROUND OF THE INVENTION

Treatment of diseased tissues by various therapies is of vital importance in the medical community. Visualization of the treatment site is preferred; however, medical advances have provided improved methods, such as cardiac catheterization, which permits a physician to perform a medical procedure on the heart without ever directly observing the treatment site.

Cardiac catheterization includes the, use of a catheter, which delivers, for example, a fiber optic cable to the treatment site. Transmission of electromagnetic energy, such as laser light, through the fiber optic cable can then be used to coagulate blood vessels or cauterize tissue via photothermal treatment. It has been found desirable to utilize photothermal treatment for a variety of diseases, including heart disease and ischemic portions of the heart muscle. Photothermal treatment involves the delivery of optical energy to the desired site and the conversion of the optical energy into thermal energy.

Photothermal treatment of tissue has certain drawbacks associated with the positioning of the catheter and the fiber optic cable. For example, the heat that is generated can cause blood in the artery, vein, or atrium to coagulate and/or form a thrombosis. This misdirected energy may also prevent the treatment site from receiving what is believed to be the appropriate dose of therapeutic energy. These drawbacks are often associated with not being able to directly or indirectly visualize the treatment site.

Generally, the catheter is visualized by use of X-rays. The opacity of the catheter and its components, in comparison to the relative transparency of body tissues and fluids, permits the physician to determine the approximate location of the catheter. This method allows for some uncertainty in the exact placement of the fiber optic cable and catheter and does not inform the physician when the catheter is in contact with tissue. Alternatively, viewing the catheter endoscopically can monitor positioning of the fiber optic cable inside a patient. However, blood and other body fluids can obstruct the view of the physician, which can lead to imprecise positioning of the catheter. Either method does not allow the physician to always predict when the distal end of the catheter is in contact with the site that requires treatment.

A need therefor exists for a method and apparatus, which overcomes and circumvents the above-identified problems. In particular, there is a need for phototherapy systems that can optimize contact and/or control the delivery of phototherapy such that radiation is delivered only when a satisfactory degree of contact is achieved.

SUMMARY OF THE INVENTION

Methods and apparatus for phototherapy are disclosed in which laser light or other radiation is projected from within a catheter, through a balloon member, and toward the surface of tissue. In one embodiment, the light is projected in an annular pattern without requiring direct contact of the energy source, e.g. a laser (via fiber), with the targeted tissue. The light reflected from body fluids or the tissue surface is captured by a collecting device located within the catheter, e.g., within the balloon member, and the intensity of the reflected light (or a ratio of reflected light at certain wavelengths) is ascertained. Quantification of the reflected light provides the operator with information to determine when the catheter if positioned at the treatment site.

The balloon member of the catheter serves to force any remaining body fluids, such as blood, away from the treatment site. The absence of body fluids, such as blood, causes an increase in the amount of reflected light from the tissue surface, thereby indicating to the operator when the instrument is advantageously positioned against the treatment site. The invention is particularly useful in cardiac therapy in creating annular conduction blocks in atrial chamber tissue, e.g. centered about but at a defined distance from a pulmonary vein orifice or coronary sinus orifice, to eliminate aberrant wave conduction.

The invention is particularly useful for inducing phototherapeutic processes in tissue, including ablation and/or coagulation of the tissue. Typically the optical apparatus is contained within a catheter including a flexible elongate member having a proximal end, a distal end and at least one longitudinal lumen extending therebetween. The distal end of the flexible elongate member can be open or includes a transparent cap, a centering balloon, or a centering coil. The optical apparatus of the invention can be fixed at a distal location or preferably disposed within the first lumen in a manner that permits axial motion within the lumen. The optical apparatus serves to project light through, or from, the distal end of the flexible member of the catheter. The optical apparatus can include an optical fiber and other light projecting elements.

In certain embodiments, the optical apparatus of the invention is slidably positioned within the lumen of a catheter proximate to a tissue site. Positioning the optical apparatus at the particular location within the;balloon and/or by adjusting the size or shape of the balloon permits control over the size and distance of the forwardly projected light. In a preferred embodiment, the light is projected in an annular fashion as is described in pending U.S. patent application Ser. No. 09/602,420, filed Jun. 23, 2000, entitled "Phototherapeutic Waveguide Apparatus", attorney docket number 101327-147, now allowed, which claims priority to U.S. patent application Ser. No. 09/357,355 filed on Jul. 14, 1999, now U.S. Pat. No. 6,423,055 the contents of which are incorporated herein by reference. This control permits the annular beam of projected light to be dynamically changed to specifically target the atrial tissue surrounding the pulmonary veins or coronary sinus.

In certain embodiments, the tissue forms a lumen, e.g., vascular, atrial, ventricular, arterial, venous, brachial, or urethral lumen. Preferably the methods include projecting an annular light pattern via an optical apparatus that is located at a defined distance from the target tissue.

In one embodiment of the present invention, the photoablation instrument includes an expandable balloon member adapted to surround the optical assembly upon inflation. Injection of a solution or gas expands the balloon, thereby forcing blood and/or other body fluids from the tissue site. Preferably, the balloon member can be inflated with deuterium oxide or deuterated water, such that the inflated balloon provides a low loss transmission pathway for radiation between the optical assembly and the tissue surface. Deuterium oxide provides the advantage that it absorbs less energy from the transmitted energy, thereby preventing the balloon from becoming heated.

The optical apparatus, projects light through the catheter and balloon toward a tissue surface. Reflected light from the surrounding area is then captured by a collector. This "feedback" array is in communication with spectrophotometers and a computer, which can be used to determine when the instrument is positioned correctly at the treatment site. A region of tissue can then be exposed to radiation from the optical assembly both for determining whether the instrument is positioned properly as well as therapeutic treatment. The methods of the invention can be performed therapeutically or prophylactically.

BRIEF DESCRIPTION OF THE DRAWINGS

Other objects, advantages and features of the present invention will be readily appreciated as the same becomes better understood by reference to the following detailed description when considered in connection with the accompanying drawings, in which like reference numerals designate like parts throughout the figures thereof and wherein.

DETAILED DESCRIPTION OF THE INVENTION

Figure 1:
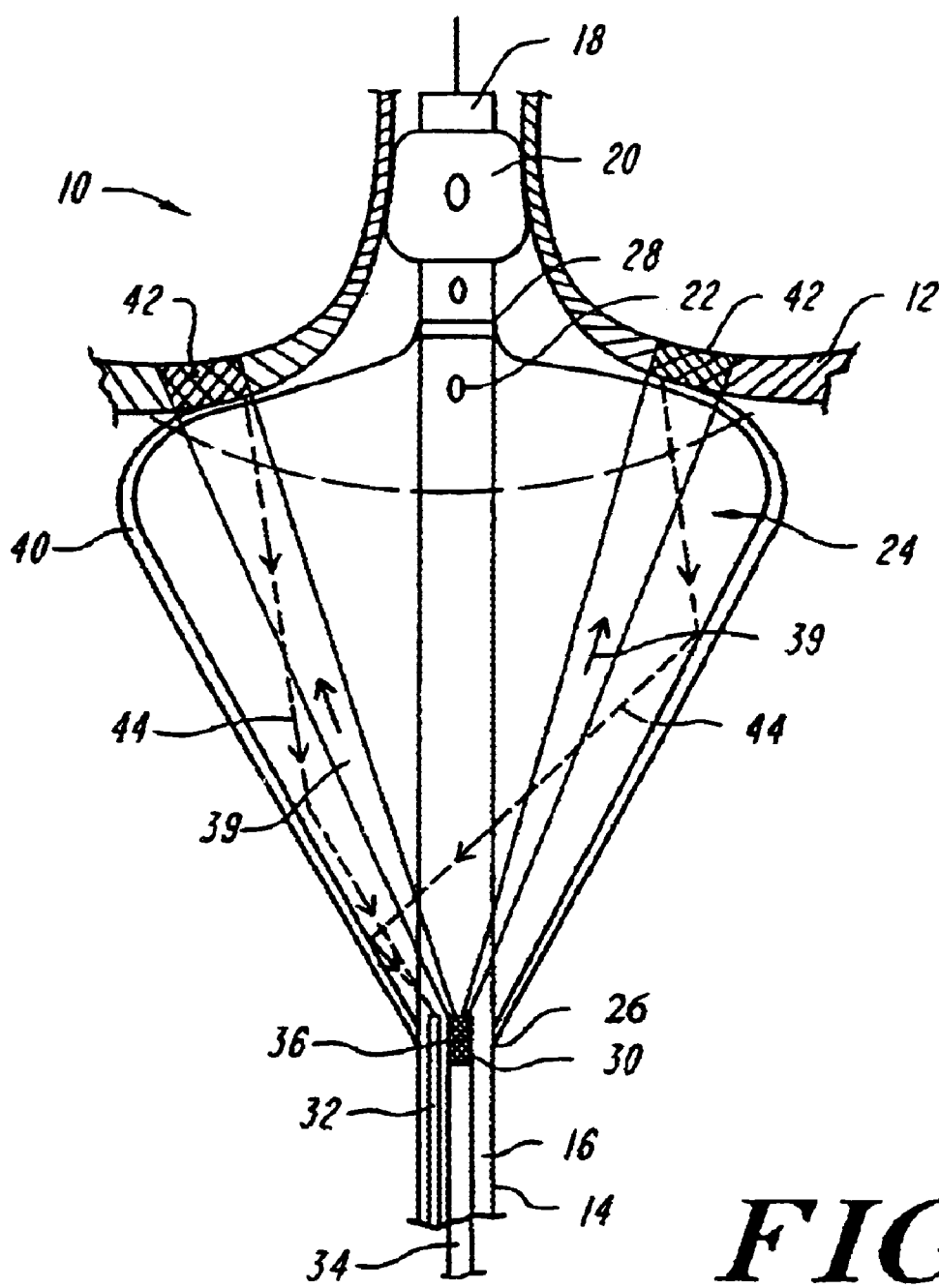
FIG. 1 is a schematic perspective view of an optical apparatus of the invention that projects an annular beam of light for both positioning the apparatus and for delivery of therapeutic energy.

The features and other details of the invention will now be more particularly described and pointed out in the claims. It will be understood that the particular embodiments of the invention are shown by way of illustration and not as limitations of the invention. The principle features of this invention can be employed in various embodiments without departing from the scope of the invention.

The present invention is based, at least in part, on a discovery that the present invention can be used for inducing hyperthermia, coagulation or phototherapeutic processes in tissue, e.g., ablation, degradation, or destruction of tissue, at a specified site in tissue without harming the surrounding tissue. The results are surprising and unexpected since the efficiency and efficacy of coherent light is generally diminished by light scatter, formation of "hot spots" due to inefficient light scatter, by the limitation that the light emitted from an optical fiber continues in a straight path, and/or from interaction(s) with blood and/or body fluids which surround a tissue site to be treated. Generally, electromagnetic radiation, e.g., light, is projected from an optical apparatus within a catheter toward a tissue surface for therapeutic treatment. It has now been found that measurement of reflected light, or the lack thereof, from body fluids or tissue, at certain wavelengths provides an operator with the ability to accurately position a catheter containing an optical apparatus at a treatment site.

Prior to this invention, the energy emitter of electromagnetic radiation, e.g., a laser source, ultraviolet light, microwave radiation, radio-frequency, etc., has generally been required to be in contact with the tissue to effect a therapeutic or prophylactic treatment. In contrast to known apparatuses and methods, the present invention does not require direct contact between the energy source, e.g., a laser source, and the tissue site to be treated. The electromagnetic radiation, e.g., coherent light can be projected annularly, diffusedly via a diffusive tip assembly known in the art, or in a forward direction. Moreover, in certain embodiments the methods and apparatus of the invention circumvent the drawbacks of having blood or body fluid coagulate, degrade or be destroyed in the treatment area proximate to the targeted tissue due to interactions with the applied energy.

Typically the physician must visualize the location of the flexible elongate member, e.g., a catheter, by use of X-ray imaging. The opaque catheter is visualized under X-ray imaging and can be followed as the catheter is positioned within a lumen. This method allows for inaccurate placement of the catheter near the treatment site. The physician is hindered in knowing whether the catheter is accurately positioned so that a therapeutic treatment can be undertaken. Alternatively, an endoscope can be inserted into the lumen to visualize the treatment field. However, blood and body fluids often impede visualization of the treatment site and accurate placement of the catheter to the site is not effected.

The present invention provides the ability to position the flexible elongate member and optical assembly at the treatment site such that contact with the tissue is achieved. This ability is based on reflectance measurements of light scattered or absorbed by blood, body fluids and tissue. For example, white light projected from the optical assembly toward tissue has several components including red and green light. Red-light has a wavelength range of about 600 to about 700 nanometers (nm) and green light has a wavelength range of about 500 to about 600 nm. When the projected light encounters blood or body fluids, most if not all green light is absorbed and hence very little green or blue light will be reflected back toward the optical assembly which includes a reflected light collector. As the apparatus is positioned such that blood and body fluids are removed from the treatment field cleared by an inflated balloon member, the reflectance of green and blue light increases as biological tissue tends to reflect more green light. As a consequence, the amount of reflected green or blue light determines whether there is blood between the apparatus and the tissue or not.

For example, as the instrument is positioned in a heart chamber, the green-blue reflectance signal should remain nearly at zero until contact with the surface of the heart tissue. When the inflated balloon member contacts the heart tissue, green light is reflected back into the optical assembly and the collector. In one embodiment, only green light is projected toward the tissue surface. In another embodiment, red and green light are both projected toward the tissue surface. The red and green light can be transmitted simultaneously or separately. The use of both red and green light provides the advantage that there is no requirement that the operator needs to know how much light must be transmitted into the balloon toward the tissue surface to insure that a reflectance signal is returned. The ratio of the two different wavelengths can be measured. For example, the instrument can measure reflectance of both green light and red light.

When the intensity of the light is sufficient, reflected red light is detected throughout the positioning process. Prior to contact of the instrument, and more specifically the inflated balloon, with the tissue the ratio of red light to green light would be high. Upon contact with the tissue, the ratio drops since more light is reflected from the tissue without any intervening blood to absorb the green light.

The reflected light is transmitted back through a collector, such as an optical fiber to a spectrophotometer. The spectrophotometer (Ocean Optics Spectrometer, Dunedin, Fla., model S-2000) produces a spectrum for each reflected pulse of reflected light. Commercially available software (LabView Software, Austin, Texas) can isolate values for specific colors and perform ratio analyses. In a preferred embodiment, the optical fiber serves as both the illuminator as well as the collector. Generally at least one optical fiber is used to transmit the electromagnetic radiation. Preferably, one or more optical fiber collectors are used to receive the reflected light. The collectors can be positioned about the optical fiber illuminator to assess whether a portion of the balloon has not contacted the tissue area with sufficient force to remove any unwanted blood or body fluids.

By use of multiple optical fiber collectors positioned about the lumen of the catheter, the operator can determine in which plane the catheter and balloon should be adjusted to minimize blood between the optical assembly and the treatment site. A suitable optical fiber or collector is described in U.S. Pat. No. 6,071,302, issued to Edward Sinofsky on Jun. 6, 2000, the contents of which are incorporated herein by reference. Once the operator is satisfied with the positioning of the instrument, electromagnetic radiation, e.g., laser radiation can be emitted onto the tissue site via a separate optical fiber or, preferably, through the same optical fiber used to transmitting the white, green or red light. The laser light can be pulsed intermittently in synchronous fashion with the positioning/reflecting light.

The present invention is drawn to an apparatus for inducing phototherapeutic processes in tissue. These processes can include ablation and/or coagulation. Typically the optical apparatus is contained within a catheter including a flexible elongate member having a proximal end, a distal end and a longitudinal first lumen extending therebetween. The distal end or a portion of the distal end of the flexible elongate member is open, transparent, includes a transparent cap or an anchoring balloon. The optical apparatus of the invention can be slidably extended within the first lumen for projecting light through or from a distal end portion of the flexible member, and preferably through a balloon member.

In one aspect, the present invention provides an optical apparatus of the invention that includes a pattern-forming optical waveguide for projecting an annular beam of light and a light transmitting optical fiber. Radiation is propagated through the optical fiber, which is in communication with a waveguide. The waveguide is configured to forwardly project an annular light pattern such that an annular lesion is formed in tissue. Typically, the annular light pattern is projected at an angle between about 20 and 45 degrees from the center plane of the optical fiber. In one embodiment, the annular light pattern expands over distance and is in the form of a ring or a halo. Preferably, the optical apparatus further includes a graded intensity lens (GRIN) adjacent to the optical waveguide for imaging the light pattern.

The present invention provides the advantage that an annular light pattern is forwardly projected. The invention further provides that the angle of projection can be adjusted by a combination of either a GRIN lens, a waveguide, a conical reflector, and/or by the dimensions of a balloon, described infra, located proximate to the optical apparatus. The present invention further provides the advantage of a "feedback reflectance" system, described herein, that instructs the operator as to when the treatment field is cleared of blood and when the apparatus is in contact with the treatment site based on the intensity of reflected light. Thus, the present invention, provides a beam of energy, e.g., coherent light, which is projected forwardly onto a tissue surface without interference of blood of body fluids. This in turn provides the advantage that the optical assembly/apparatus remains separated from the treatment site. Typically, the optical assembly is positioned from about 14 mm to about 24 mm, preferably from about 16 mm to about 22 mm, most preferably from about 20 mm to about 24 mm from the tissue site with the beam of light projected forwardly over a distance of from about 14 mm to about 24 mm, preferably from about 16 to about 22 mm, most preferably from about 20 mm to about 24 mm.

In contrast to the present invention, conventional laser ablation devices rely upon on contact with target tissue sites or the projection of a focused spot of radiation. Such prior art devices can not create an annular ring about a preselected site or vary the size and/or shape of the annulus to accommodate specific exposure constraints. In addition, the present invention can project ablative energy onto a specific site, unlike cryogenic or sonic techniques that treat a site along with tissue that surrounds the site due to energy dissipation about the treatment site. The use of the reflectance feedback system of the invention further provides the advantage over conventional therapies of determining when the apparatus is most accurately located about the tissue site.

The terms "optical assembly" or "optical apparatus" is intended to include various combinations of optical fibers, lenses, waveguides, reflectors, reflected light collectors and other optical elements.

The term "phototherapeutic" is intended to include photoablative, photochemical and photothermal processes that are therapeutic and/or prophylactic in a subject.

The terms "ablate" or "ablation" or "photothermal" are well recognized in the art and are intended to include thermal coagulation and/or removal of biological tissue. Ablation also includes the desiccation of tissue by the application of heat. For example, an ablating energy, such as those described above, would be one that would cause the tissue to reach a temperature of between about 50–90° C. Ablation increases the physiological temperature of a tissue by energetic stimulation to a temperature that degrades or eradicates tissue, thereby removing diseased tissue from a localized area. Ablation can be used as a therapeutic treatment, where diseased or otherwise unwanted tissue or cells exist, or as a preventative treatment to inhibit exigent physiological aberrations, e.g., arrhythmias e.g., fibrillations or flutters, growth of undesirable tissue or cells in a specific region of an organ or viscera. In order to obtain destruction of tissue exclusively by thermal effects, it is necessary for the energy to be able to reach a threshold of destruction referred to as the "thermal dose." This threshold is a function of temperature reached and of the duration of the application. Therefore, ablation, to some degree, is based on the rise of the local temperature of tissue.

The term "coagulation" is well recognized in the art and is intended to mean the action whereby cells and/or body fluids within a treated tissue site are caused to become necrotic, thickened and/or lacking in the ability to conduct electrical activity, thereby resulting in a coherent mass by the methods of the invention. The method and apparatus of the invention permit selective, coagulation of a targeted tissue area and not blood or other body fluids which are found external, e.g., surrounding, to the target site.

The term "body fluids" is intended to encompass those naturally occurring physiological components produced by a subject to maintain stasis. These fluids typically include physiological components such as plasma, growth factors, platelets, lymphocytes, granulocytes, etc.

The terms "into" and "onto" are used interchangeably and are intended to include treatment of tissue by focusing energy, e.g., ablative, coagulative, or photothermal, toward the afflicted area. In some instances the energy penetrates the tissue and in other instances the energy only superficially treats the surface of the tissue. An ordinary skilled artisan would understand what depths of penetration are required and those parameters that are dependent upon the application, tissue type, area to be treated and severity of condition. Accordingly, the amount of energy used to treat the afflicted area would be attenuated based upon the disease or condition-being treated.

The term "waveguide" is well recognized in the art and is intended to include those devices that constrain or guide the propagation of electromagnetic radiation along a path defined by the physical construction of the guide. Although optical waveguides in the form of optical fibers are preferred, other types of waveguides can be used to transmit electromagnetic radiation. Several waveguides are of importance, including hollow-pipe waveguides and dielectric waveguides. Hollow-pipe guides are used primarily in the microwave region of the spectrum, dielectric guides primarily in the optical region. Various guide shapes are possible, including circular, triangular, rectangular, or square and combinations thereof.

Waveguides can be made from materials known in the art such as quartz, fused silica or polymers such as acrylics. Suitable examples of acrylics include acrylates, polyacrylic acid (PAA) and methacrylates, polymethacrylic acid (PMA). Representative examples of polyacrylic esters include poly-methylacrylate (PMA), polyethylacrylate and polypropylacrylate. Representative examples of polymethacrylic esters include polymethylmethacrylate (PMMA), polyethylmethacrylate and polypropylmethacrylate.

Internal shaping of the waveguide can be accomplished by removing a portion of material from a unitary body, e.g., a cylinder or rod. Methods known in the art can be utilized to modify waveguides to have tapered inner walls, e.g., by grinding, milling, ablating, etc. Preferably, a hollow polymeric cylinder, e.g., a tube, is heated so that the proximal end collapses and fuses together, forming an integral proximal portion, which tapers to the distal end of the waveguide. In a preferred embodiment, the waveguide is flexible.

The term "annular" is used to describe various circumferential or ring-like patterns including circular, elliptical, polygonal and irregular shapes. The annulus is preferably a closed figure but in certain applications an open (e.g. "C"-shaped) or discontinuous annular pattern can be useful or preferred.

In preferred embodiments, the electromagnetic radiation, e.g., coherent light, is emitted from the waveguide such that the projected energy expands over a distance. For example, annular projection of laser light from a circular waveguide forms an expanding cone. The angle of the cone of light is dependent upon the angle of reflection within the waveguide, the concavity of inner walls within the waveguide and the distance to an object to which it is projected. For example, an optical apparatus can include an optical fiber in communication with an optical waveguide having a concave interior. The waveguide passes an annular beam of light to a GRIN lens. The beam that exits from distal portion of the waveguide will expand over a distance, di. Typically, the angle of projection from the central axis of the optical fiber or waveguide is between about 20 and 45 degrees.

In preferred embodiments, the electromagnetic radiation, e.g., coherent light, is emitted through the optical fiber through the optional GRIN lens and onto a conical reflector such that the projected energy expands uniformly over a distance. For example, annular projection of laser light from a conical reflector forms an expanding cone. The angle of the cone of light is dependent upon the angle of conical reflector and the distance to an object to which it is projected. Typically, the angle of projection from the central axis of the optical fiber is between about 20 and 45 degrees.

The terms "gradient index lens" or "graded index lens" (GRIN) are well recognized in the art and are intended to mean those lenses which have a refractive index distribution, which takes place in a parabolic manner so that the refractive index is greatest at the central axis of the rod and so that the refractive index is progressively reduced from the central axis toward the periphery of the rod. As a result, the light is focused. The shape of the RIN lens can be cylindrical, oval, round, or convex.

The term "flexible elongate member" is well recognized in the art and is intended to refer to a hollow tube having at least one lumen. In general, a flexible elongate member is often termed a "catheter", a term which is well known in the art. The flexible elongate member has proximal and distal ends with at least one longitudinal lumen extending therebetween. The distal end can be open or closed as is known in the art. In one embodiment, the distal end of the flexible elongate member is open, thereby allowing an optical apparatus of the invention to protrude beyond the elongate member, e.g., into a catheter end, e.g., into a balloon member. In another embodiment, the distal portion of the elongate member is closed, thereby preventing an optical apparatus from passing beyond the distal end of the elongate member.

Preferably, the materials used to construct the flexible elongate member or the catheter end portion are "transparent" materials, such as fluoropolymers. Suitable transparent materials include polyether block amides (PEBAX), polyethylene, nylon, polyurethanes and silicone containing polymers, e.g., silastic. Suitable fluoropolymers include, for example, fluorinated ethylene propylene, (FEP), perfluoroalkoxy resin (PFA), polytetrafluoroethylene (PTFE), and ethylene-tetrafluoroethylene (ETFE). Typically the diameter of the flexible elongate member is between about 0.050 inches and about 0.104 inches, preferably between about 0.060 inches and about 0.078 inches. The diameter of at least one inner lumen of the flexible elongate member is between about 0.030 inches and about 0.060 inches, preferably between about 0.040 inches and about 0.050 inches. The length of the flexible elongate member varies with the intended application and in generally between about 60 cm and about 145 cm in length. For cardiac applications the flexible elongate member is between about 80 cm, and about 125 cm long, for bronchial applications the flexible elongate member is 125 cm long.

The term "catheter" as used herein is intended to encompass any hollow instrument capable of penetrating body tissue or interstitial cavities and providing a conduit for selectively injecting a solution or gas, including without limitation, venous and arterial conduits of various sizes and shapes, bronchioscopes, endoscopes, cystoscopes, culpascopes, colonscopes, trocars, laparoscopes and the like. Catheters of the present invention can be constructed with biocompatible materials known to those skilled in the art such as those listed supra, e.g., silastic, polyethylene, Teflon, polyurethanes, etc.

Typically, the optical apparatus of the invention is positioned proximate to the tissue targeted for treatment within a catheter. The catheter has been positioned proximate to the targeted tissue site and provides that the optical apparatus can be slidably positioned proximate to the tissue, thereby avoiding direct contact with the tissue and/or body fluids. In a preferred embodiment, a balloon is inflated against the tissue, thereby forcing blood and/or body fluids away from the tissue targeted for treatment. Positioning light energy is then passed through the optical apparatus and balloon onto the targeted tissue such that light, e.g., an annular image, is projected onto the site. The light reflected, if any, is collected via a collector, e.g., an optical fiber, and is analyzed to determine whether the catheter and balloon are accurately positioned at the tissue site. Light energy is then passed through the optical apparatus, which causes ablation, coagulation and/or phototherapeutic processes to occur within the tissue. The therapeutic light energy can be passed through the optical apparatus simultaneously with the positioning light via either a separate optical fiber or through the same optical fiber. Optionally, the therapeutic light and positioning light can be passed through the same optical fiber in pulsed duration such that the pulses are synchronized. Alternatively, once the apparatus is accurately positioned, the positioning light energy can be discontinued and only the therapeutic light energy can be projected onto the tissue site.

The terms "about" or "surrounding" when used in conjunction with the term "a coronary vessel opening" is intended to describe the atrial surface surrounding the blood vessel mouth or orifice inside the heart. Similarly, the term "about the pulmonary vein" is intended to encompass the atrial surface surrounding the pulmonary vein and/or its orifice. "Cardiac vessels" include without limitation, the pulmonary veins, the coronary sinus, the inferior vena cava and the superior vena cava. The exposed (ablated) areas preferably do not include any interior portion of the coronary vessels in order to minimize the risk of inadvertent stenosis.

The term "fixedly attached" is intended to include those methods known in the art to attach a catheter end portion, cap, or balloon to the distal portion of a flexible elongate member. Various means are known to those skilled in the art for fixedly attaching individual members of the present apparatus to each other. Such methods include thermal welding or glueing the two materials together to form a uniform seam, which will withstand stresses, placed upon the integral seam. For example, the catheter end portion or a tip is welded, e.g., thermal, photochemical, sonically, e.g., ultrasound, or glued, at the proximal most portion of the catheter end or tip to the distal end of the flexible elongate member. In another embodiment, the proximal end of the catheter end is affixed to the distal end of the elongate member which is itself a sealed, e.g., having a tip or a cap.

The terms "tip" or "cap" are well recognized in the art and are intended to include those devices which are used to seal the end of a luminal body. In one embodiment, the cap is non-metallic. In certain embodiments, the cap is non-porous. In a preferred embodiment, the cap is non-metallic and non-porous, e.g., a polymeric material.

The term "catheter end portion" is intended to include a separate attachable, and in certain embodiments, detachable, catheter-like portion which is located proximate to the distal end of a catheter. The catheter end portion can be fixedly attached or integrally locked into place on the distal end of a catheter by methods known in the art, e.g., glueing, melting, ultrasonic welding, "snap on" fittings, male-female fittings, etc. Preferably the catheter end portion is energy transparent. An example of a catheter end portion is a silicone balloon anchor.

The term "control handle" is well recognized in the art and is intended to include various means to manipulate the apparatus of the invention, including at least the flexible elongate member, guidewires if present, and the optical apparatus. Various control handles useful with the present invention are commercially available, such as those manufactured by Cordis Webster, Inc., 4750 Littlejohn St., Baldwin Park, Calif., 91706. When used, the control handle applies tension, e.g., stress, to the proximate end of a guidewire, thereby causing the distal end of the guidewire to bend, distort or deform. As a consequence of this action, the flexible elongate member to which the guidewire is attached, also bends, distorts or deforms in the same plane as the guidewire.

The phrase "light transmitting optical fiber" is intended to include those fibers, glass, quartz, or polymeric, which conduct light energy in the form of ultraviolet light, infrared radiation, or coherent light, e.g., laser light.

An exemplary manufacturing process suitable for joining the waveguide or GRIN lens, for example, to a glass-clad or polymer-clad optical fiber having an outer diameter of about 50 to 1,000 micrometers can begin by stripping off a buffer from the end of the fiber, e.g., exposing about 2 or 3 millimeters of the inner fiber core and its cladding. (It is not necessary to strip the cladding away from the core.) Prior to stripping, the fiber end face preferably should be prepared and polished as is known in the art to minimize boundary or interface losses.

In one embodiment, a transparent tubular structure will form a housing and attaching means for the waveguide or GRIN lens and prepared fiber end. The fiber and waveguide or GRIN lens are positioned such that they located so that the distal end of the stripped fiber and the proximal end of the waveguide are in communication. The tubular structure can be slid over the two components, thereby fixing the respective ends to each other. Preferably, a GRIN lens is placed in communication with the distal end of the waveguide or a conical reflector is placed in communication with the distal end of the GRIN lens and contained within the tubular structure. In one preferred embodiment, the housing is a Teflon® FEP or PET tubing available, for example, from Zeus Industries (Raritan, N.J.).

Preferred energy sources include laser light, in the range between about 200 nanometers and 2.6 micrometers. In particular, wavelengths that correspond to, or are near, water absorption peaks are often preferred. Such wavelengths include those between about 805 nm and about 1060 nm, preferably between about 900 nm and 1000 nm, most preferably, between about 940 nm and 980 nm. Suitable lasers include excimer lasers, gas lasers, solid state lasers and laser diodes. A particularly preferred AlGaAs diode array, manufactured by Optopower, Tucson, Ariz., produces a wavelength of 980 nm. A preferred energy is coherent light, e.g., laser light, in the range between about 200 nm to about 2.4 micrometers, preferably between about 400 to about 3,000 nm, more preferably between about 805 and 1060 nm. Typically the optical apparatus emits between about 10 to about 25 watts of power to yield an energy fluence of ablative radiation at the heart tissue surface of about 0.5 watts/cm$^2$ to about 3 watts/cm$^2$. Alternative energy sources can include radiofrequency, ultrasound, microwave energy, thermal conductors, electrical currents and cyrogenic energy.

In one embodiment, the optical apparatus can extend beyond the distal end of the flexible elongate member. In certain embodiments, the optical apparatus slidably extends into the space created by a balloon filled with a suitable solution or gas. Alternatively, the optical apparatus can be slidably located or fixed within a transparent flexible elongate member about which surrounds an inflated balloon. In this embodiment, the light is projected annularly through the transparent flexible elongate member, through an inflation solution, e.g., deuterium oxide, and into the inflated balloon and onto the targeted treatment site.

The light transmitting optical fiber transmits the energy from an energy source, which is in communication with the optical fiber. Suitable energy sources are known in the art and produce the above-mentioned types of energy. Preferred laser sources include diode lasers. The optical fiber is positioned within lumen formed by a flexible elongate member (described supra). The optical fiber can be slidably controlled within the lumen such that positioning of the optical fiber within the flexible elongate member is readily achieved. Preferably, the optical fiber is positioned proximate to the expanded balloon member.

The balloon, e.g., a biocompatible balloon, is affixed to the catheter body member near the distal end and is in fluid communication with at least one of inflation port. Upon injection of solution such as deuterium oxide, the expandable balloon inflates forming a lumen or "reservoir" between the catheter body and the outer wall of the balloon. It should be understood that the term "balloon" encompasses deformable hollow shapes which can be inflated into various configurations including balloon, circular, tear drop, etc., shapes dependent upon the requirements of the body cavity.

In preferred embodiments useful in cardiac therapy, the balloon is configured such that energy is not applied into the pulmonary vein. As such, the distal region of the balloon is larger than the diameter of the pulmonary vein, thus permitting intimate contact with the atrial surface about the proximal region of the pulmonary vein. In a preferred embodiment, the balloon has a tear drop shape or a shape in which the distal end of the balloon is larger than the proximal end. The diameter of the distal portion of the balloon corresponds to the maximum diameter of the annularly projected light, thereby enabling the artisan to ablate tissue about the attial surface in a lesion equivalent to the diameter of the distal portion of the balloon. This configuration prevents ablation of tissue within the pulmonary vein and provides the advantage of avoiding stenosis of the pulmonary vein.

The terms "treat," "treatment" or "treating" are intended to include both prophylactic and/or therapeutic applications. The methods of the invention can be used to protect a subject from damage or injury caused by a disease, physical aberration, electrical aberration, or can be used therapeutically or prophylactically treat the subject after the onset of the disease or condition.

The term "subject" is intended to include mammals susceptible to diseases, including one or more disease related symptoms. Examples of such subjects include humans, dogs, cats, pigs, cows, horses, rats and mice.

The term "tissue" is well recognized in the art and is intended to include extracorporeal materials, such as organs, e.g., mesentery, liver, kidney, heart, lung, brain, tendon, muscle etc.

The term "modulate" includes effect(s) targeted tissue(s) that prevent or inhibit growth of diseased tissue, which may ultimately affect the physiological well being of the subject, e.g., in the context of the therapeutic or prophylactic methods of the invention.

The term "modify" is intended to encompass-those changes to the targeted tissue site, e.g., the surface, that cause the tissue to no longer have undesired properties. For example, treatment of the anterior wall of the right atrium by the present invention changes the path of electrical conduction after photonic treatment. The result is a conduction block that redirects conduction through the tissue and prevents the conduction from traveling across the atrial wall as it did prior to treatment.

The present invention also pertains to methods for forming an annular lesion in a tissue by ablation, coagulation and/or phototherapeutic processes. The methods introduce an optical apparatus proximate to a tissue site via, for example, a catheter and utilize feedback control based on reflectance of light or absorbance of light from blood, body fluids and tissue surface. The optical apparatus generally includes a modified optical waveguide that is in communication with a light transmitting optical fiber. Energy is transmitted through the optical fiber, such that radiation propagating through the optical fiber and waveguide projects an annular light pattern, e.g., a circle, ring, halo or an outline or a shape formed by and projected from the modified waveguide. Preferably, the light is projected through a graded intensity lens that is adjacent to the optical waveguide. This additional step attenuates aberrations in the light pattern and facilitates the forward annular projection of the therapeutic light. By these methods, an annular lesion can be formed in tissue. In certain embodiments, the tissue forms a lumen, e.g., vascular, atrial, brachial, urethral, ureteral, etc.

In a preferred embodiment, a balloon is inflated against the tissue, thereby forcing blood and/or body fluids away from the tissue targeted for treatment. Positioning light energy is then passed through the optical apparatus and balloon onto the targeted tissue such that light, e.g., an annular image, is projected onto the site. The light reflected, if any, is collected via a collector, e.g., an optical fiber, and is analyzed to determine whether the catheter and balloon are accurately positioned at the tissue site. Light energy is then passed through the optical apparatus, which causes ablation, coagulation and/or phototherapeutic processes to occur within the tissue.

In another aspect, the invention includes methods for treating cardiac arrhythmia(s) by introducing a photoablation instrument into the heart, positioning the photoablation instrument in a location within the heart and exposing a region of heart tissue to radiation from the optical assembly. Again, the positioning of the instrument is crucial and the ability to position the instrument by utilizing the feedback system described herein provides advantages over those therapeutic methods currently known.

The photoablation instrument includes an optical assembly for projecting a beam of radiation as described supra and infra. One advantage of this method lies in the ability to project light from the optical assembly onto cardiac tissue within the heart in, for example, an annular pattern. Another advantage of the method is that the instrument can be positioned a distance proximate to the treatment site, thereby reducing the risk of overheating the tissue area. Consequently, this method of the invention can be used to treat, for example, the pulmonary vein, coronary sinus, inferior vena cava and superior vena cava. This method of the invention can also be useful in treating cardiac tissue associated with cardiac irregularities, e.g. arrhythmias, such as the pulmonary vein, coronary sinus, inferior vena cava and superior vena cava.

Arrhythmias, for example, can occur in the atrium or ventricle, and are referred to, respectively, as atrial fibrillation and ventricular fibrillation. Atrial fibrillation is an atrial arrhythmia characterized by rapid randomized contractions of the atrial myocardium, causing an irregular, often rapid heart rate. Three of the most common types of atrial arrhythmia are ectopic atrial tachycardia, atrial fibrillation and atrial flutter. Ventricular fibrillation is an arrhythmia characterized by fibrillary contractions of the ventricular muscle due to rapid repetitive excitation of the myocardial fibers without coordinated contraction of the ventricles.

Atrial fibrillation and atrial flutter are abnormalities in the rhythm or rate of the heart beat. For an adult at rest, the heart normally beats between 60 and 80 beats per minute, but when atrial fibrillation occurs, the atria may beat irregularly and very rapidly between 350 and 600 times per minute. This causes the ventricles to beat irregularly in response as they try to keep up with the atria. Atrial flutter is similar to atrial fibrillation. The atrial contractions are less rapid, however, usually between 200 to 400 beats per minute, and are regular. Atrial flutter is often-associated with a heart attack or may occur after heart or lung surgery. Atrial fibrillation often results from a myriad of heart conditions such as angina, tachycardia, heart attack, heart valve problems, and even high blood pressure. All of these conditions can cause stretching and scarring of the atria that interfere with the heart conduction system. The heart muscle can be weakened if episodes lasting several months or longer (with rapid heart rates) occur. Briefer episodes only cause problems if the heart rate is very fast or if the patient has a serious heart problem in addition to the atrial fibrillation.

The present invention further pertains to methods for forming annular lesions in cardiac tissue, e.g., trabecular tissue, by ablation, coagulation and/or phototherapeutic processes. The methods include introduction of an optical apparatus proximate to cardiac tissue via, for example, a catheter. The optical apparatus includes an optical waveguide in communication with a light transmitting optical fiber, optionally a separate illuminator optical fiber, preferably, a GRIN lens and a collector device, e.g., an optical fiber. In a preferred embodiment, a balloon is inflated against the tissue, thereby forcing blood and/or body fluids away from the tissue targeted for treatment. Positioning light energy is then passed through the optical apparatus and balloon onto the targeted tissue such that light, e.g., an annular image, is projected onto the site. The light reflected, if any, is collected via a collector, e.g., an optical fiber, and is analyzed to determine whether the catheter and balloon are accurately positioned at the tissue site. Therapeutic energy is then transmitted through an optical fiber, such that radiation propagated through the optical fiber, waveguide and GRIN lens forwardly projects an annular light pattern, e.g., a circle or a halo. By these methods, an annular lesion can be formed in cardiac tissue.

The term "trabecular" is well recognized in the art and is intended to include tissue, e.g., cardiac tissue, which is a elastic tissue often formed of bands and cords called trabeculae consisting of fibrous tissue, elastic fibers and muscle fibers.

In one embodiment, the method of the invention can be utilized to treat ventricular tachycardia by projecting an annular beam onto the ventricular tissue. The annular beam focuses energy onto the tissue and forms a lesion. The lesion forms a conduction block and impedes electrical conduction through the formerly problematic tissue, thereby preventing further abnormal electrical stimulation in the afflicted cardiac tissue.

In FIG. 1, apparatus 10, constructed in accordance with the present invention, is depicted in its expanded form within a body cavity such as an atrial surface 12. Flexible elongate member 14 includes at least one lumen 16 extending the length thereof from a proximal end to a distal end and can include, optionally, cap 18 and/or an anchoring balloon 20. Openings 22 in the side wall of the flexible elongate member 14 define one or more pores that provide fluid communication between the lumen 16 and a balloon 24, which can be bonded at proximal end 26 and distal end 28 to flexible elongate member 14. Optical apparatus 30 can be slideably positioned within lumen 16 adjacent to balloon 24. Apparatus 10 can further include reflectance fiber 32 to monitor the progress of treatment as described throughout the specification. Optical apparatus 30 can include optical fiber 34, a modified waveguide 36 and, optionally, a GRIN lens (not shown) which projects light 39 in a forward, and preferably, annular fashion. Alternatively, optical apparatus 30 includes optical fiber 34, optionally, a GRIN lens (not shown) and a conical reflector (not shown) that projects light in a forward or annular fashion.

In a preferred embodiment, an energy reflecting sheath 40 surrounds a portion of the balloon 24. The energy reflecting sheath 40 is generally made of a polymeric material, such a polyethylene terephthalate, with scattering particles contained therein. Suitable scattering particles include silicon oxide, titantium oxide, aluminum oxide and bismuth oxide Typically, the energy reflecting sheath 40 is attached about the flexible elongate member 14 and covers approximately one third to one half of balloon 24 in a hemispherical arrangement. Preferably, the energy reflecting sheath 40 covers balloon 24 up to the portion of the balloon which contacts the tissue surface, for example, at a point of contact designated as 42. The energy reflecting sheath 40 serves to capture and return reflected light 44 from the tissue surface onto reflectance fiber 32, thereby increasing the sensitivity of the collecting fiber 32 of the apparatus 10.

Injection of fluid or gas, through lumen 16 and pores 22, forces the fluid or gas to flow out of the pores 22 to fill the chamber 38 within balloon 24, thereby inflating balloon 24. Generally, a solution is preferred, e.g., water, saline, or, preferably, deuterium oxide to inflate balloon 24.

In a preferred embodiment, the outer balloon 24 is spherical, parabolic, or teardrop shaped. Preferably, flexible elongate member 14 and balloon 24 are energy transparent. Optical apparatus 10 can be slidably positioned within lumen 16 adjacent to balloon 24. Gas, e.g., air, or a liquid can be injected through a separate lumen to inflate silicone balloon anchor 20 if required.

The devices described in FIG. 1 can be used for treating, e.g., ablating, coagulating and/or phototherapeutically treating, endocardial surfaces which promote arrhythmias or other disease states or conditions. For example, atrial therapies can be performed by inserting an apparatus of the invention 10 into the femoral vein, Flexible elongate member 14 having balloon 24 fixedly attached is guided through the inferior vena cava, and into the right atrium, and if required, it is guided into the left atrium via atrial septal puncture. Left ventricular treatment can be performed by inserting flexible elongate member 14 into the femoral artery. Flexible elongate member 14 is guided through the iliac artery, the aorta, through the aortic valve and adjacent to the wall of the left ventricle. Once balloon 24 is proximate to the tissue ablation site, a solution can be injected through lumen 16 to force blood and/or body fluids away from the treatment site. Optical apparatus 30 is guided through flexible member 14 via lumen 16 to a position proximate to the tissue ablation site. Positioning light 39 is emitted through optical fiber 34 and captured by a collecting device, such as a reflectance fiber 32. Optionally, reflectance fiber 32 and optical fiber 24 can serve as both light emitter and collector. Light energy 39 is then emitted through balloon 24 via optical fiber 34, as described above, or through a separate optical fiber. Preferably, the composition of flexible elongate member 14 and balloon 24 are transparent to the energy emitted through optical apparatus 10.

Figure 2:
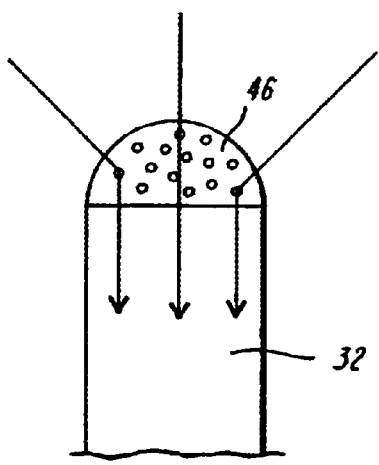
FIG. 2 is a cut away view of a preferred optical fiber that can serve as both light emitter and reflected light collector.

FIG. 2 depicts an optical fiber 34 that can serve as both an energy emitter for positioning light and therapeutic light as well as a reflectance fiber 32. The optical fiber 34 is a wide aperture collecting fiber that is described in U.S. Pat. No. 6,071,302, the contents of which are incorporated herein by reference. For example, reflected light 44 is captured from the tip 46 of 34.

In another aspect of the invention, a real-time display means can be incorporated into a surgical microscope or goggles worn by a clinician, during the procedure or displayed on a monitor to provide a visual display of contact between the balloon 24 and the tissue treatment site simultaneously with the viewing of the surgical site. The display can reveal reflectance values at one or more specific wavelengths (preferably, chosen for their sensitivity to the onset and optimal state of tissue modification), as well as display a warning of loss of optimum contact between the balloon 24 and tissue and/or provide for automatic shut-off.

In one method, according to the invention, application of laser to a biological structure(s) occurs while the reflectance of light from the irradiated site is monitored. Changes in positioning of the balloon 24 against the tissue site will cause a reflectance change especially when blood absorbs reflected light,44. The reflectance can be monitored in real-time to determine the optimal positioning of the apparatus 10 or aid as visual feedback in the timing used in sweeping the energy across the treatment site during the procedure.

Figure 3:
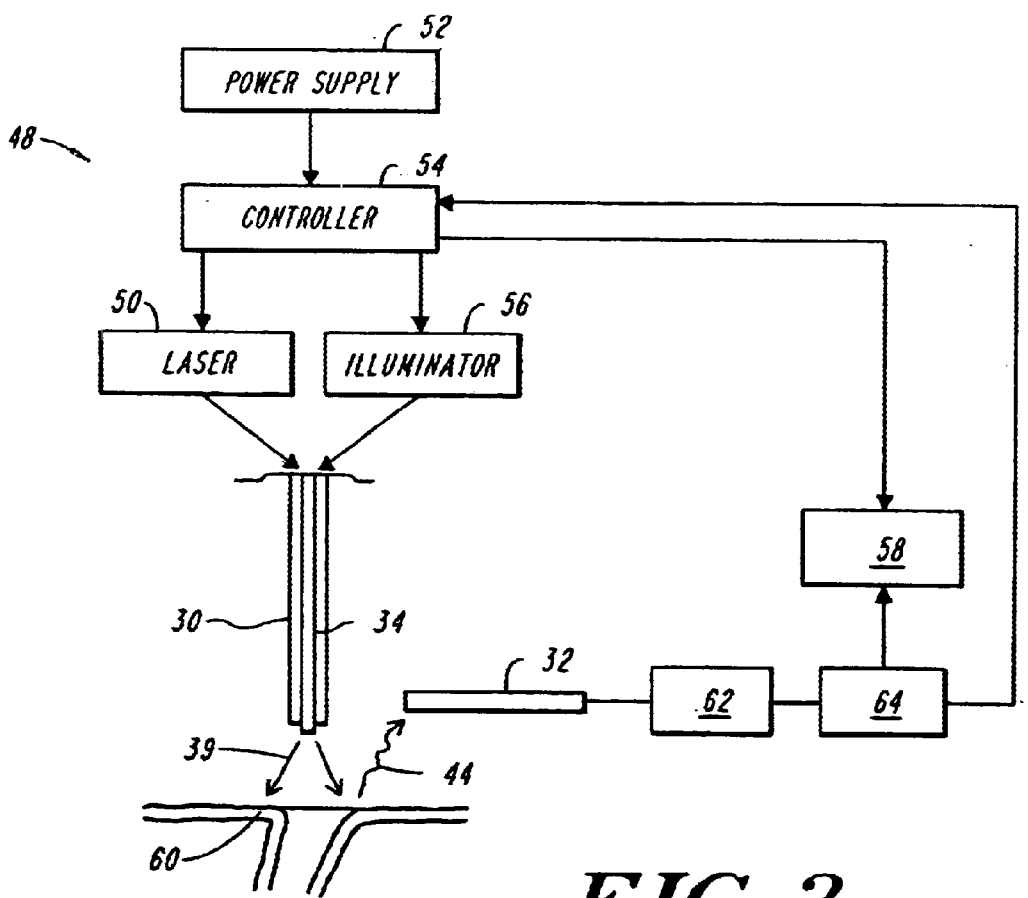
FIG. 3 is a schematic diagram of a laser tissue treatment system according to the present invention.

In FIG. 3, a schematic block diagram of a laser tissue treatment system 48 is shown, including a laser 50, power supply 52, controller 54 and reflectance reflectance fiber 32. The system further includes optical apparatus 30, an illumination source 56, and display 58. In use, the output of illuminator 56 is delivered to the treatment site 60 to illuminate the surface via light 39, preferably white or green light or red and green light, with the surface reflecting light 44 toward a reflectance fiber 32. As discussed above, the intensity or ratio of light waves can be used to determine the accuracy and proximity to the treatment site surface 60. The output of laser 50 is also delivered, preferably via optical apparatus 30, to treatment site 60 to phototherapeutically treat selected tissue.

As the laser beam irradiates treatment site 60 the biological tissue of the site is coagulated, ablated and/or phototherapeutically treated. The placement accuracy to the treatment site 60 is determined by the reflectance monitor 64 (e.g., a spectrometer), which provides electrical signals to controller 54 in order to control the procedure. The reflectance monitor 64 receives light reflected by the site from a broadband or white light illumination source 56 via fiber 34 and/or from laser 50 via optical apparatus 30. In addition to controlling the laser operation automatically, the reflectance monitor 64 and/or controller 54 can also provide signals to a display 58 to provide visual and/or audio feedback to the clinical user. Optional filter 62 can be employed to block reflected light from the laser at the therapeutic wavelength.

In one embodiment, the spectrometer 64 can be synchronized with the illumination source 56 to variably detect different wavelengths of energy at differing cycles (Hz). For example, the detector can differentiate;between a wavelength in the green light region at a cycle of 50 Hz from that of a wavelength in the red light region at 33 Hz. Additionally, therapeutic energy can also be detected at a third interval of time.

Figure 4A:
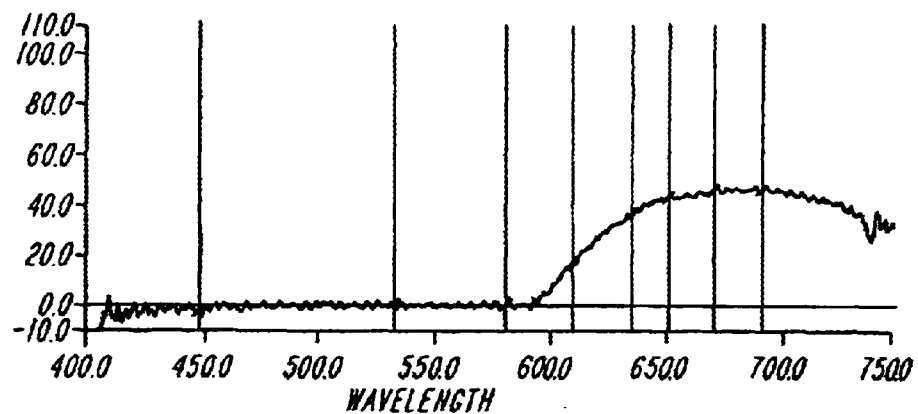
FIG. 4A is a reflectance spectrum of blood.
Figure 4B:
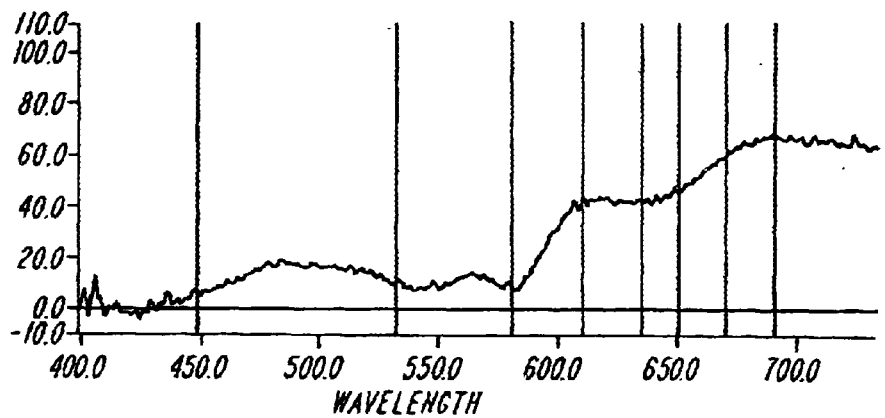
FIG. 4B is a reflectance spectrum of beef tissue.
Figure 4C:
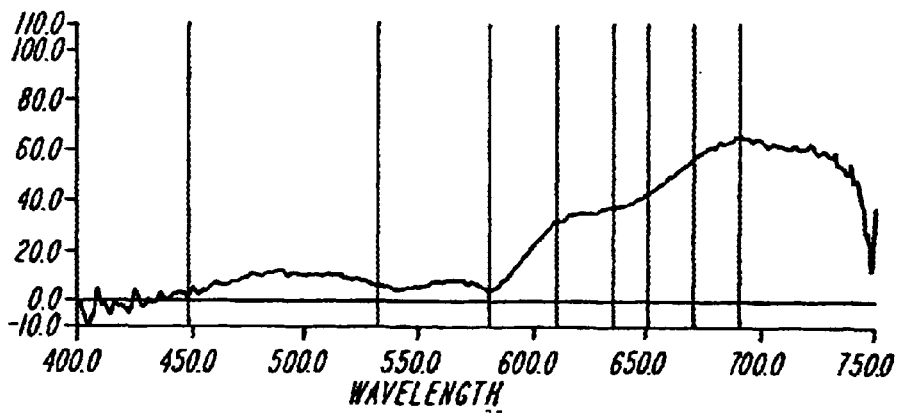
FIG. 4C is a reflectance spectrum of beef tissue and blood, where the blood has been removed under conditions simulated where a balloon catheter evacuates the area of blood and illuminating light shown onto the tissue sample is reflected.

FIGS. 4A, 4B and 4C are graphical representations of the reflectance and absorbance properties of blood, beef tissue and a beef tissue sample treated with blood where the blood has been removed under conditions simulated where a balloon of the above-described apparatus would force blood away from the tissue. In FIG. 4A, blood absorbs light with a wavelength range of 450 to about 580 nm, the blue and green spectra. FIG. 4B shows that tissue, such as beef tissue, reflects blue and green light in the ranges over 450 nm to about 525 nm and about 550 nm to about 580 nm. The reflectance intensity of green light is generally about one-third of that of red light, which is in the range of from about 600 nm to about 700 nm. FIG. 4C is a dramatic representation of how the present invention improves an operator's ability to accurately assess when a laser device is advantageously contacted with tissue, and blood is eliminated from the tissue area. For example, blood was contacted with beef tissue and a laser apparatus with a balloon was placed against the tissue to force blood away from the tissue. Illumination of the tissue surface produced the reflectance spectra of 4C. Comparison of FIG. 4C with FIG. 4B shows that the absorbencies are virtually identical, demonstrating that removal of blood from the tissue sight is critical and that the use of reflected light is useful for determining whether the instrument is properly positioned at a treatment site.

Figure 5:
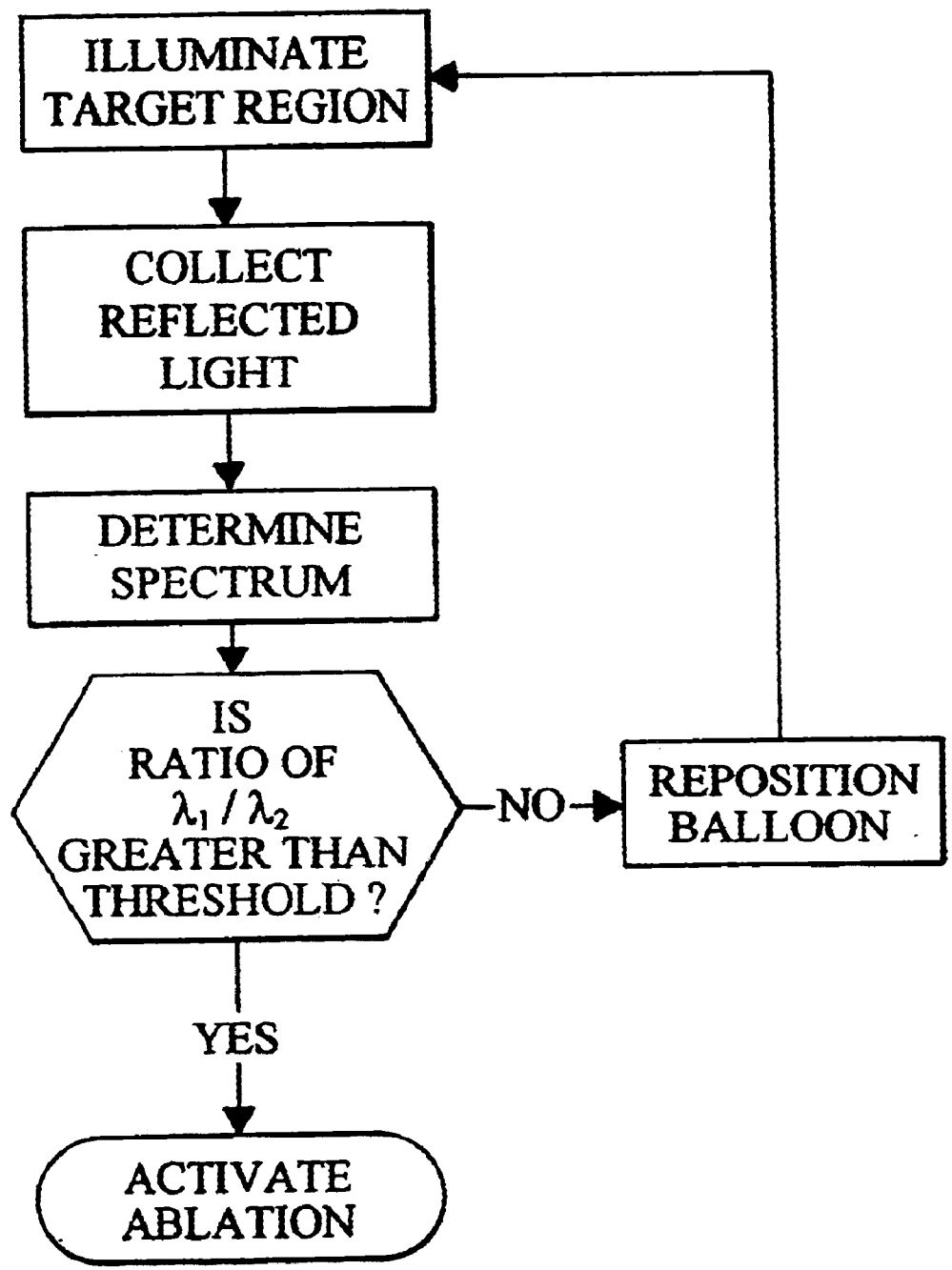
FIG. 5 is a schematic block diagram demonstrating how an operator would utilize the apparatus and method of the invention.

FIG. 5 is a schematic block diagram demonstrating how an operator would optimize the use of the apparatus and method of the invention based on maximizing the intensity or ratio of reflected light. For example, the tissue surface is illuminated via white light (which contains red and green light) or pulsed red and green light. Reflected light is collected and the spectrum determined. A ratio between the reflected green light (alpha 1) and red light (alpha 2) is determined. If, for example, blood impedes the transmission of the illuminating light, the ratio approaches or is zero. In this instance, the balloon portion of the apparatus should be repositioned to remove blood from the treatment site. As blood is removed from the light field; the ratio of green to red light is maximized, and the position of the balloon should be maintained. Once the ratio of alpha 1/alpha 2 is greater than a threshold value, ablation of the tissue can begin.

Those having ordinary skill in the art will know, or be able to ascertain, using no more than routine experimentation, many equivalents to the specific embodiments of the invention described herein. These and all other equivalents are intended to be encompassed by the following claims. All publications and references cited herein including those in the background section are expressly incorporated herein by reference in their entirety.

What is claimed is:

1. A method for determining contact with an intralumenal tissue surface, comprising the step of:
  a) positioning an intralumenal therapeutic medical device toward the intralumenal tissue surface, wherein the therapeutic medical device comprises:
    an energy delivering catheter having a flexible elongate member adapted for intralumenal positioning and a balloon member at a distal end of the elongate member, the balloon member adapted to contact tissue upon inflation within a body lumen, and further including a position-sensing system comprising:
    an illuminator disposable within balloon member that projects energy through the balloon member toward the intralumenal tissue surface; and a collecting device also disable within the balloon member which receives reflected energy tat returns to the balloon member;
  b) inflating the balloon member to contact intralumenal tissue;
  c) projecting energy toward the intralumenal tissue surface;
  d) collecting reflected energy from the intralumenal tissue surface or body fluid; and
  e) analyzing the changes in reflected energy to indicate whether the balloon member has adequately contacted the intralumenal tissue area.

2. The method of claim 1, wherein the energy is green light.

3. The method of claim 1, wherein the energy is green and red light.

4. The method of claim 1, wherein the energy is white light.

5. The method of claim 1, wherein to energy is both for location and is therapeutic.

6. The method of claim 5, wherein the therapeutic energy is phototherapeutic.

* * * * *